United States Patent
Shennib

(10) Patent No.: US 10,085,678 B2
(45) Date of Patent: Oct. 2, 2018

(54) SYSTEM AND METHOD FOR DETERMINING WHO GRADING OF HEARING IMPAIRMENT

(71) Applicant: iHear Medical, Inc., San Leandro, CA (US)

(72) Inventor: Adnan Shennib, Oakland, CA (US)

(73) Assignee: iHear Medical, Inc., San Leandro, CA (US)

(*) Notice: Subject to any disclaimer, the term of this patent is extended or adjusted under 35 U.S.C. 154(b) by 443 days.

(21) Appl. No.: 14/971,215

(22) Filed: Dec. 16, 2015

(65) Prior Publication Data

US 2016/0166181 A1  Jun. 16, 2016

Related U.S. Application Data

(60) Provisional application No. 62/092,545, filed on Dec. 16, 2014.

(51) Int. Cl.
*A61B 5/12* (2006.01)
*H04R 25/00* (2006.01)
*A61B 5/00* (2006.01)

(52) U.S. Cl.
CPC ............ *A61B 5/123* (2013.01); *A61B 5/6898* (2013.01); *A61B 5/7405* (2013.01); *H04R 25/305* (2013.01); *A61B 2560/0223* (2013.01)

(58) Field of Classification Search
CPC ....... A61B 5/0022; A61B 5/121; A61B 5/123; A61B 5/6898; A61B 5/7405; A61B 5/7415; A61B 5/7435; H04R 25/30; H04R 25/305
(Continued)

(56) References Cited

U.S. PATENT DOCUMENTS 4,759,070 A   7/1988  Voroba
5,197,332 A   3/1993  Shennib
(Continued)

FOREIGN PATENT DOCUMENTS

JP    57188235 A    11/1982
JP    06105828 A    4/1994
(Continued)

OTHER PUBLICATIONS

Amlani, et al. "Methods and applications of the audibility index in hearing aid selection and fitting." Trends in amplification 6.3 (2002): 81-129.*
(Continued)

*Primary Examiner* — David J McCrosky
(74) *Attorney, Agent, or Firm* — Dorsey & Whitney LLP

(57) ABSTRACT

Examples of systems and methods for rapidly grading the hearing of a user in accordance with WHO guidelines are disclosed. One example includes a personal computer and a test device configured to produce calibrated acoustic output at suprathreshold levels presented at an audiometric frequency range from 500 to 4000 Hz. The consumer's minimal response levels are registered, and a hearing ability score is presented to indicate a hearing grade and hearing aid candidacy. The hearing ability score may be representative of a classification of the WHO grading of hearing impairment. Systems and methods disclosed herein, with considerations for room noise present in the consumer's environment, allow for rapid hearing profiling, using a standard personal computer and minimal low-cost hardware, thus particularly suited for self-testing outside clinical environments such as at home, office, or retail store settings.

32 Claims, 11 Drawing Sheets

(58) Field of Classification Search
USPC .................................. 600/559; 381/58–60
See application file for complete search history.

(56) References Cited

U.S. PATENT DOCUMENTS

| | | | |
|---|---|---|---|
| 5,327,500 A | 7/1994 | Campbell | |
| 5,553,152 A | 9/1996 | Newton | |
| 5,645,074 A | 7/1997 | Shennib et al. | |
| 5,659,621 A | 8/1997 | Newton | |
| 5,701,348 A | 12/1997 | Shennib et al. | |
| 5,785,661 A | 7/1998 | Shennib et al. | |
| 5,928,160 A | 7/1999 | Clark | |
| 6,137,889 A | 10/2000 | Shennib et al. | |
| 6,212,283 B1 | 4/2001 | Fletcher et al. | |
| 6,319,207 B1 | 11/2001 | Naidoo | |
| 6,359,993 B2 | 3/2002 | Brimhall | |
| 6,367,578 B1 | 4/2002 | Shoemaker | |
| 6,379,314 B1 | 4/2002 | Horn | |
| 6,382,346 B2 | 5/2002 | Brimhall et al. | |
| 6,428,485 B1 | 8/2002 | Rho | |
| 6,447,461 B1 | 9/2002 | Eldon | |
| 6,473,513 B1 | 10/2002 | Shennib et al. | |
| 6,522,988 B1 | 2/2003 | Hou | |
| 6,546,108 B1 | 4/2003 | Shennib et al. | |
| 6,674,862 B1 | 1/2004 | Magilen | |
| 6,724,902 B1 | 4/2004 | Shennib et al. | |
| 6,840,908 B2 | 1/2005 | Edwards et al. | |
| 6,937,735 B2 | 8/2005 | DeRoo et al. | |
| 6,940,988 B1 | 9/2005 | Shennib et al. | |
| 6,978,155 B2 | 12/2005 | Berg | |
| 7,016,511 B1 | 3/2006 | Shennib | |
| 7,037,274 B2 | 5/2006 | Thoraton et al. | |
| 7,113,611 B2 | 9/2006 | Leedom et al. | |
| 7,215,789 B2 | 5/2007 | Shennib et al. | |
| 7,260,232 B2 | 8/2007 | Shennib | |
| 7,298,857 B2 | 11/2007 | Shennib et al. | |
| 7,310,426 B2 | 12/2007 | Shennib et al. | |
| 7,321,663 B2 | 1/2008 | Olsen | |
| 7,403,629 B1 | 7/2008 | Aceti et al. | |
| 7,424,123 B2 | 9/2008 | Shennib et al. | |
| 7,424,124 B2 | 9/2008 | Shennib et al. | |
| 7,580,537 B2 | 8/2009 | Urso et al. | |
| 7,664,282 B2 | 2/2010 | Urso et al. | |
| 7,854,704 B2 | 12/2010 | Givens et al. | |
| 7,945,065 B2 | 5/2011 | Menzl et al. | |
| 8,073,170 B2 | 12/2011 | Kondo et al. | |
| 8,077,890 B2 | 12/2011 | Schumaier | |
| 8,155,361 B2 | 4/2012 | Schindler | |
| 8,184,842 B2 | 5/2012 | Howard et al. | |
| 8,243,972 B2 | 8/2012 | Latzel | |
| 8,284,968 B2 | 10/2012 | Schumaier | |
| 8,287,462 B2 | 10/2012 | Givens et al. | |
| 8,379,871 B2 | 2/2013 | Michael et al. | |
| 8,396,237 B2 | 3/2013 | Schumaier | |
| 8,447,042 B2 | 5/2013 | Gurin | |
| 8,467,556 B2 | 6/2013 | Shennib et al. | |
| 8,503,703 B2 | 8/2013 | Eaton et al. | |
| 8,571,247 B1 | 10/2013 | Oezer | |
| 8,718,306 B2 | 5/2014 | Gommel et al. | |
| 8,798,301 B2 | 8/2014 | Shennib et al. | |
| 9,031,247 B2 | 5/2015 | Shennib | |
| 9,060,233 B2 | 6/2015 | Shennib et al. | |
| 9,107,016 B2 | 8/2015 | Shennib | |
| 9,326,706 B2 | 5/2016 | Shennib | |
| 2001/0008560 A1 | 7/2001 | Stonikas et al. | |
| 2001/0009019 A1 | 7/2001 | Armitage | |
| 2001/0051775 A1 | 12/2001 | Rho | |
| 2002/0027996 A1 | 3/2002 | Leedom et al. | |
| 2002/0085728 A1 | 7/2002 | Shennib et al. | |
| 2003/0007647 A1 | 1/2003 | Nielsen et al. | |
| 2003/0078515 A1 | 4/2003 | Menzel et al. | |
| 2004/0028250 A1 | 2/2004 | Shim | |
| 2005/0094822 A1 | 5/2005 | Swartz | |
| 2005/0226447 A1 | 10/2005 | Miller, III | |
| 2005/0245991 A1 | 11/2005 | Faltys et al. | |
| 2005/0249370 A1 | 11/2005 | Shennib et al. |
| 2005/0259840 A1 | 11/2005 | Gable et al. |
| 2005/0283263 A1 | 12/2005 | Eaton et al. |
| 2006/0210104 A1 | 9/2006 | Shennib et al. |
| 2006/0291683 A1 | 12/2006 | Urso et al. |
| 2007/0076909 A1 | 4/2007 | Roeck et al. |
| 2007/0189545 A1 | 8/2007 | Geiger et al. |
| 2007/0223721 A1 | 9/2007 | Stern et al. |
| 2007/0237346 A1 | 10/2007 | Fichtl et al. |
| 2008/0240452 A1 | 10/2008 | Burrows et al. |
| 2008/0273726 A1 | 11/2008 | Yoo et al. |
| 2009/0103764 A1 | 4/2009 | Stiehl et al. |
| 2010/0040250 A1 | 2/2010 | Gerbert |
| 2010/0119094 A1 | 5/2010 | Sjursen et al. |
| 2010/0145411 A1 | 6/2010 | Spitzer |
| 2010/0191143 A1 | 7/2010 | Ganter |
| 2010/0239112 A1 | 9/2010 | Howard et al. |
| 2010/0268115 A1 | 10/2010 | Wasden et al. |
| 2010/0284556 A1 | 11/2010 | Young |
| 2011/0058697 A1 | 3/2011 | Shennib et al. |
| 2011/0100127 A1 | 5/2011 | Beck |
| 2011/0176686 A1 | 7/2011 | Zaccaria |
| 2011/0188689 A1 | 8/2011 | Beck et al. |
| 2011/0190658 A1 | 8/2011 | Sohn et al. |
| 2011/0200216 A1 | 8/2011 | Lee et al. |
| 2011/0206225 A1 | 8/2011 | Møller et al. |
| 2011/0237103 A1 | 9/2011 | Harlan et al. |
| 2012/0051569 A1 | 3/2012 | Blamey et al. |
| 2012/0130271 A1 | 5/2012 | Margolis et al. |
| 2012/0157876 A1 | 6/2012 | Bang et al. |
| 2012/0177212 A1 | 7/2012 | Hou et al. |
| 2012/0177235 A1 | 7/2012 | Solum |
| 2012/0183164 A1 | 7/2012 | Foo et al. |
| 2012/0183165 A1 | 7/2012 | Foo et al. |
| 2012/0189140 A1 | 7/2012 | Hughes |
| 2012/0213393 A1 | 8/2012 | Foo et al. |
| 2012/0215532 A1 | 8/2012 | Foo et al. |
| 2012/0302859 A1 | 11/2012 | Keefe |
| 2013/0010406 A1 | 1/2013 | Stanley |
| 2013/0177188 A1 | 7/2013 | Apfel et al. |
| 2013/0243227 A1 | 9/2013 | Kinsbergen et al. |
| 2013/0243229 A1 | 9/2013 | Shennib et al. |
| 2013/0294631 A1 | 11/2013 | Shennib et al. |
| 2014/0003639 A1 | 1/2014 | Shennib et al. |
| 2014/0150234 A1 | 6/2014 | Shennib et al. |
| 2014/0153761 A1 | 6/2014 | Shennib et al. |
| 2014/0153762 A1 | 6/2014 | Shennib et al. |
| 2014/0254843 A1 | 9/2014 | Shennib |
| 2014/0254844 A1 | 9/2014 | Shennib |
| 2015/0023512 A1 | 1/2015 | Shennib |
| 2015/0023534 A1 | 1/2015 | Shennib |
| 2015/0023535 A1 | 1/2015 | Shennib |
| 2015/0025413 A1 | 1/2015 | Shennib |
| 2015/0215714 A1 | 7/2015 | Shennib et al. |
| 2016/0066822 A1 | 3/2016 | Shennib et al. |

FOREIGN PATENT DOCUMENTS

| | | |
|---|---|---|
| JP | 2002191581 A | 7/2002 |
| JP | 2005168856 A | 6/2005 |
| JP | 2008109594 A | 5/2008 |
| KR | 1020050114861 A | 12/2005 |
| KR | 1020100042370 A | 4/2010 |
| WO | 99/07182 A2 | 2/1999 |
| WO | 2006136174 A2 | 12/2006 |
| WO | 2010/091480 A1 | 8/2010 |
| WO | 2011128462 A2 | 10/2011 |
| WO | 2015009559 A1 | 1/2015 |
| WO | 2015009561 A1 | 1/2015 |
| WO | 2015009564 A1 | 1/2015 |
| WO | 2015009569 A1 | 1/2015 |

OTHER PUBLICATIONS

Second Office Action for JP Application No. 2016-526994, dated Oct. 31, 2017.
Internet Archive, World Health Organization website "Grades of Hearing Impairment". Retrieved from <https://web.archive.org/web/

(56) References Cited

OTHER PUBLICATIONS

20121024120107/http://www.who.int/pbd/deafness/hearing_impairment_grades/en> on Aug. 27, 2015.
"Basic Guide to In Ear Canalphones", Internet Archive, Head-Fi.org, Jul. 1, 2012. Retrieved from http://web.archive.org/web/20120701013243/http:www.head-fi.org/a/basic-guide-to-in-ear-canalphones> on Apr. 14, 2015.
"dB HL—Sensitivity to Sound—Clinical Audiograms", Internet Archive, AuditoryNeuroscience.com, Apr. 20, 2013. Retrieved from. <https://web.archive.org/web/20130420060438/http://www.auditoryneuroschience.com/acoustics/clinical_audiograms>on Apr. 14, 2015.
"Lyric User Guide", http://www.phonak.com/content/dam/phonak/b2b/C_M_tools/Hearing_Instruments/Lyric/documents/02-gb/Userguide_Lyric_V8_GB_FINAL_WEB.pdf, Jul. 2010.
"Methods for Calculation of the Speech Intelligibility Index", American National Standards Institute, Jun. 6, 1997.
"Specification for Audiometers", American National Standards Institute, Nov. 2, 2010.
"The Audiogram", Internet Archive, ASHA.org, Jun. 21, 2012. Retrieved from <https:/web.archive.org/web/20120621202942/http://www.asha.org/public/hearing/Audiogram> on Apr. 14, 2015.
"User Manual—2011", AMP Personal Audio Amplifiers.
Abrams, "A Patient-adjusted Fine-tuning Approach for Optimizing the Hearing Aid Response", The Hearing Review, Mar. 24, 2011, 1-8.
Amlani, et al., "Methods and Applications of the Audibility Index in Hearing Aid Selection and Fitting", Trends in Amplication 6.3 (2002) 81. Retrieved from <https://www.ncbi.nim.nih.gov/pmc/articles/PMC4168961/> on Apr. 14, 2015.
Asha, "Type, Degree, and Configuration of Hearing Loss", American Speech-Language-Hearing Association; Audiology Information Series, May 2011, 1-2.
Convery, et al., "A Self-Fitting Hearing Aid: Need and Concept", http://tia.sagepubl.com, Dec. 4, 2011, 1-10.
Franks, "Hearing Measurements", National Institute for Occupational Safety and Health, Jun. 2006, 183-232.
Kiessling, "Hearing aid fitting procedures—state-of-the-art and current issues", Scandinavian Audiology vol. 30, Suppl 52, 2001, 57-59.
Kryter, "Methods for the calculation and use of the articulation index", The Journal of the Acoustical Society of America 34.11 (1962): 1689-1697. Retrieved from <http://dx.doi.org/10.1121/1.1909094> on Aug. 27, 2015.
NHANES, "Audiometry Procedures Manual", National Health and Nutrition Examination Survey, Jan. 2003, 1-105.
Sindhusake, et al., "Validation of self-reported hearing loss. The Blue Mountains hearing study", International Journal of Epidemiology 30.6.(2001): 1371-1378. Retrieved from <http://ije.oxfordjournals.org/content/30/6/1371.full> on Aug. 27, 2015.
Traynor, "Prescriptive Procedures", www.rehab.research.va.gov/mono/ear/traynor.htm, Jan. 1999, 1-16.
World Health Organization, "Deafness and Hearing Loss", www.who.int/mediacentre/factsheets/fs300/en/index.html, Feb. 2013, 1-5.

\* cited by examiner

SYSTEM AND METHOD FOR DETERMINING WHO GRADING OF HEARING IMPAIRMENT

CROSS-REFERENCE TO RELATED APPLICATION(S)

This application claims the benefit under 35 U.S.C. 119 of the earlier filing date of U.S. Provisional Application No. 62/092,545 entitled "METHOD FOR RAPIDLY DETERMINING WHO GRADING OF HEARING IMPAIRMENT," filed Dec. 16, 2014. The aforementioned provisional application is hereby incorporated by reference in its entirety, for any purpose.

This application is related to U.S. Pending patent application Ser. No. 14/011,620, titled "HEARING PROFILE TEST SYSTEM AND METHOD," filed on Aug. 27, 2013; and Ser. No. 14/846,003, titled "HEARING TEST SYSTEM FOR NON-EXPERT USER WITH BUILT-IN CALIBRATION AND METHOD," filed on Sep. 4, 2015; all of which are also incorporated herein by reference, in their entirety, for any purpose.

TECHNICAL FIELD

Examples described herein relate to methods and systems of hearing grading, particularly for rapidly profiling the hearing ability of a person, and for determining hearing aid candidacy according to WHO guidelines.

BACKGROUND

The World Health Organization (WHO) is a specialized agency of the United Nations that is concerned with international public health. A user at the primary level may not be trained to assess hearing loss nor how audiological equipment should be calibrated and maintained.

WHO defines disabling hearing impairment in adults as a permanent unaided hearing threshold level (average for frequencies 0.5, 1, 2, 4 kHz) for the better ear of 41 dB or greater. WHO classifies hearing impairment into 5 grades ranging from no or slight hearing problems to unable to hear and understand even a shouted voice. The 5 grades encompass distinct ranges of hearing loss and each grade has an associated hearing aid indication (recommendation). WHO suggests that hearing aids may be needed for those with slight hearing impairment, and more strongly recommends hearing aids for higher levels of impairment. WHO grades of 2, 3, and 4 are classified as disabling hearing impairment.

WHO hearing impairment grading is determined according to the hearing threshold, which is the lowest intensity at which sound is just audible to a person. The hearing testing method required for determining WHO hearing impairment grading is essentially an audiogram test. The instrumentation and accessories for standard audiometric evaluation are generally specialized electro-medical devices for use in a clinical setting. For example, to obtain a valid audiogram report, tests are generally performed in specialized sound-isolated rooms, often referred to as a "sound booth," to reduce noise levels present in the environment in order to test hearing ability down to 0 or −10 dB HL (see, e.g., ANSI S3.1: American Standard Maximum Permissible Ambient Noise Levels for Audiometric Rooms). The combined cost of a sound booth and clinical instrumentation for standard audiogram testing can easily exceed $20,000.

Performing a hearing assessment is generally not practical for lay people to self-administer or administer to others, particularly in home, office, or retail store settings. Even in quiet room environments, noise levels typically exceed the maximum level allowed for determining the threshold of hearing. Another limitation for hearing test administration outside clinical settings is the complexity associated with the test procedure, which can be perplexing and time consuming for a lay person. Further, conducting a test and hearing threshold search in 5 dB increments, as defined by standard audiometric methods is relatively time-consuming and results do not convey a hearing aid indication to a consumer.

Current hearing evaluation methods and associated reports are generally designed for administration and interpretation by hearing professionals, such as an audiologist, an otolaryngologist, a hearing aid dispenser, etc. Audiogram results are generally of little value to a lay consumer and generally present irrelevant information pertaining to hearing aid candidacy. The audiogram test report, generally considered the standard form for hearing assessment and hearing aid prescription, is technical and not suitable for interpretation by a potential hearing aid consumer. For example, an audiogram report generally presents a person's hearing sensitivity for tonal sounds from −10 to 110 dB, inversely displayed, versus test frequencies from 125 to 8000 Hz. Although hearing sensitivity for each frequency may also be tabulated in other audiogram forms, they are generally not useful for a lay consumer, particularly for indicating hearing aid candidacy. Furthermore, determining the hearing ability in certain level ranges, such as −10 to +15 dB HL, is generally not relevant to a person's ability to carry on normal conversations. Another barrier for performed hearing assessment by a non-expert is related to the aforementioned cost, complexity and inaccessibility of standard hearing test instruments.

To circumvent some of the limitations of standard hearing evaluation methods, automated, computer-based hearing evaluation methods have been proposed, including self-administered online tests using personal computers and smartphones. These tests are often inadequate due to their inaccuracy caused by audio characteristics of consumer electronics not meeting the standards of audiometric testing. In addition to the aforementioned obstacles related to audio characteristics, the calibration of acoustic signals emanating from a consumer transducer (a consumer earphone or a speaker, for example) represents a daunting challenge, preventing accurate hearing evaluation by the lay consumer using a personal computer, or a personal electronic device.

Hearing screening tests offer basic hearing assessment for individuals on the basis of a pass or fail criteria. Generally speaking, these tests are administered by a hearing professional or a nurse, using a portable instrument, which produces a limited set of test stimuli often at a predetermined level between 20 and 40 dB HL depending on the age of the group being tested. A major drawback of current hearing screening methods is the lack of sensitivity and specificity for determining the hearing ability and indicating hearing aid candidacy. As a result, "failed" subjects are generally referred to a hearing professional for further hearing assessment prior to hearing aid candidacy assessment and hearing aid fitting.

SUMMARY

The present disclosure describes example systems and methods for automatic hearing grading and indicating hearing aid candidacy, substantially in accordance with World Health Organization (WHO) guidelines, without resorting to conventional 5 dB step audiometry and clinical settings.

More specifically, the systems and methods disclosed herein utilize a set of test stimuli at levels generally above 15 dB HL and in step levels in the range of 10-20 dB, for rapid hearing grading in non-clinical settings, such as in a home, a senior center, a community center, a retail store, a pharmacy, or an office as examples. The computerized hearing test is rapid and easy to self-administer, or to administer by a lay person, with accurate test results.

In some examples, the hearing grading system may include a computing device, for example a personal computer or a smartphone, and a test device communicatively coupled to the computing device. The test device may include an audio signal generator for generating calibrated audio signals to administer the hearing grading in the user's environment, such as a home or office. In some examples, the test device may be worn on the body or placed on a table during the hearing grading. The hearing ability test presents a sequence of suprathreshold test stimuli, generally above 15 dB HL with increments in the range of 10-25 dB, up to a test level of approximately 81-95 dB HL.

Sequences of test stimuli may be provided to an ear of the user. The test stimuli may comprise test stimuli levels within a suprathreshold range of 15 dB to 95 dB HL. Each of the sequences may comprise test stimuli at test frequencies comprising 500, 1000, 2000, and 4000 Hz. The test stimuli levels may comprise a first test level in the range of 15-25 dB HL; a second test level in the range of 30-40 dB HL; a third test level in the range of 45-55 dB HL; and a fourth test level in the range of 65-75 dB HL. The sequence of test stimuli may be provided at nonuniform step levels. Each step level may be within the range of 10-25 dB.

The consumer's minimum response level (MRL) within the suprathreshold sound level range presented at each test frequency band may be registered using the computing device. The computing device may execute a hearing test software application to implement the hearing profiling method described herein, and to present a hearing ability score representative of the general hearing ability and a hearing aid indication. The hearing ability score is representative of the WHO grading of hearing impairment. The hearing ability score is computed based on an average of minimal response levels only within the suprathreshold range presented at each of the test frequencies.

In some examples, the delivery of the acoustic test signal from the hearing grading system may be provided by a consumer-type earphone with calibrated electroacoustic performance. The earphone may be provided with insert eartips, to occlude the ear canal and reduce the audibility of ambient background noise present in typical room environments. By limiting the test presentations to suprathreshold levels, generally exceeding 15 dB HL, and using ear occluding eartips, hearing grading substantially in accordance with WHO grading guidelines may be performed in any reasonably quiet room environments using the method of the present invention, eliminating the cost and inconvenience of specialized audiometric earphones and clinical settings. In an example embodiment, a microphone is incorporated within the test device to sense the level of ambient background noise and pause the hearing evaluation process as may be necessary accordingly. Using systems and methods disclosed herein, a non-expert person may administer, or self-administer a hearing grading method that is easy to understand and evaluates hearing aid candidacy according to the WHO guidelines without resorting to costly and complex standard audiometric procedures.

BRIEF DESCRIPTION OF THE DRAWINGS

The above objectives, features, aspects and attendant advantages of the present invention will become apparent from the following detailed description of various embodiments, including the best mode presently contemplated of practicing the invention, when taken in conjunction with the accompanying drawings, in which.

DETAILED DESCRIPTION OF PREFERRED EMBODIMENTS

Certain details are set forth below to provide a sufficient understanding of embodiments of the invention. Some embodiments, however, may not include all details described herein. In some instances, some well-known structures may not be shown, in order to avoid unnecessarily obscuring the described embodiments of the invention.

Figure 1:
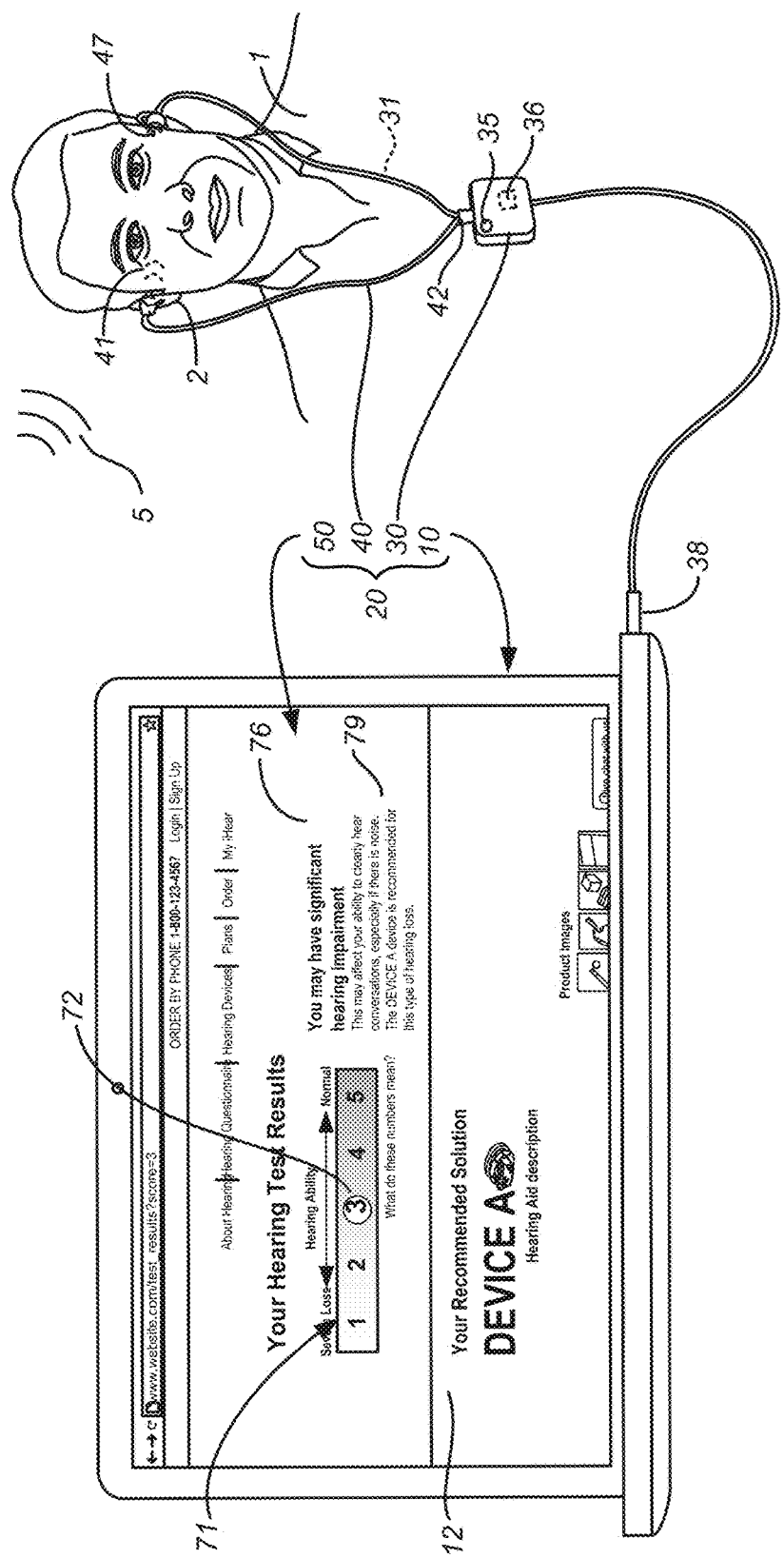
FIG. 1 is a view of a computerized hearing grading system, including a test device comprising an audio signal generator for generating test signals, a personal computer and an earphone for producing test stimuli, according to some examples.

The present disclosure describes example systems and methods, as shown in FIGS. 1-11, for rapidly and inexpensively determining a hearing grading and indicating hearing aid candidacy according to the World Health Organization (WHO) guidelines without requiring expensive equipment and clinical settings. Referring to FIG. 1, in some examples, the evaluation process may use a generic computing device, for example a personal computer 10, in conjunction with a handheld test device 30 configured to generate a calibrated test audio signal 31 to earphones 40 to administer a hearing grading in the consumer's environment, such as a home, office, or retail store. The personal computer 10, the test device 30, hearing grading software application 50, and the earphones 40 may collectively form a computerized test system 20 (also referred to herein as "computerized hearing grading system" and "hearing grading system"). The computerized test system 20 may present a sequence of suprathreshold test stimuli 41, generally above 15 dB HL, into the ear 2 of the test subject 1. For reference purposes, 0 HL represents the threshold of hearing for normal hearing individuals, and suprathreshold refers to sound levels above the threshold of normal hearing. In an example embodiment, 25 dB may be used as the minimal test level, which represents a significant increase over normal threshold levels, from the sound level perspective, as well as electrical signal requirements for the audio test signal 31 producing the acoustic test stimuli 41. In some examples, the test stimuli 41 may be provided in step levels in the range of 10-25 dB, in contrast to conventional audiometric methods which specify 5 dB increments for threshold determination. In some examples, the algorithm for determining the hearing impairment grade involves step levels of the test stimuli that are nonuniform.

Table 1 shows the WHO grading of hearing impairment and corresponding hearing ability scores, according to some examples. The WHO grading of hearing impairment may relate to remediation after the acquisition of hearing loss. The audiometric ISO values shown in Table 1 are averages of hearing loss values at 500, 1000, 2000, and 4000 Hz. The WHO grading of hearing impairment may grade hearing impairment based on an inability to hear sounds of a certain level of intensity.

audiometry with 5 dB level increments, only a single test level is presented within the WHO grading range for each test frequency, resulting in a reduced set of test stimuli for a rapid hearing grading method.

Figure 2:
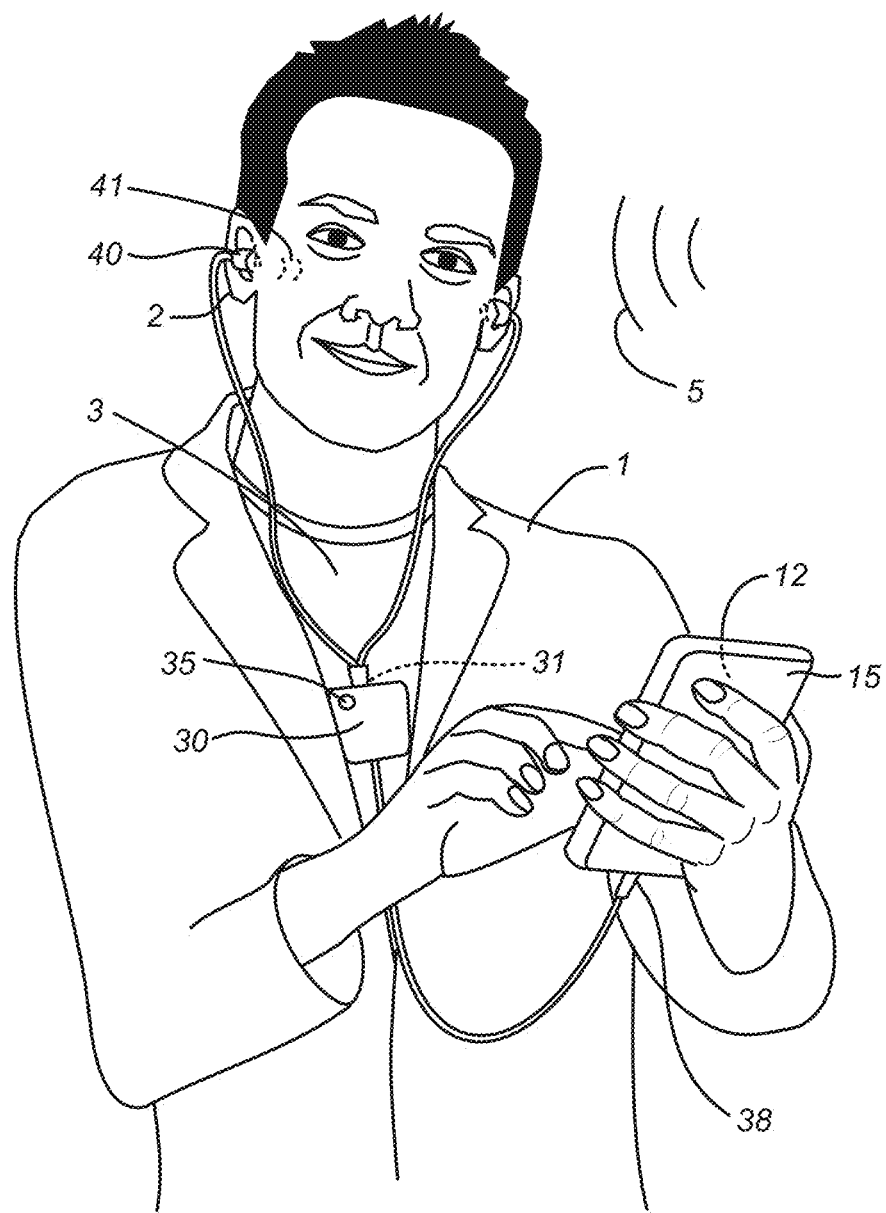
FIG. 2 is a representation of a hearing grading system using a smart phone and a test device clipped on the shirt of a user, according to some examples.

FIG. 2 shows an example smartphone embodiment, with a body-worn test device 30 connected to smartphone 15 for executing a hearing grading application for self-administration. The user 1 follows instructions and registers audibility responses using the touch screen 12 or a key of the smartphone 15. Similarly, a hearing ability score 72, hearing profile statement 76, and hearing aid candidacy 79 are presented to the user following the hearing grading. The computerized hearing grading system 20 is implemented to enable rapid and sufficiently accurate assessment of a consumer's hearing ability in environments outside clinical setting, and to provide an easy to understand scoring system with hearing ability scale 71 and hearing aid candidacy scale 78.

In some examples, the test stimuli 41 is presented at four frequency bands within the audiometric frequency range of about 500 to 4000 Hz. The user's minimum response level (MRL) within the suprathreshold (with respect to normal hearing) range at each test frequency band may be registered using the personal computer's standard interface, such as a keyboard, mouse, or touch screen 12. The personal computer 10 may also be in the form of a smartphone 15 as shown in FIG. 2, or a tablet computer (not shown). A personal computer 10 herein generally refers to any personal com-

TABLE 1

| Hearing Ability Score | World Health Organization (WHO) Grading of Hearing Impairment | | | |
|---|---|---|---|---|
| | Grade of impairment | Audiometric ISO value | Performance | Recommendations |
| 5 | 0 - No impairment | 25 dB or better (better ear) | No or very slight hearing problems. Able to hear whispers. | |
| 4 | 1 - Slight impairment | 26-40 dB (better ear) | Able to hear and repeat words spoken in normal voice at 1 meter. | Counseling. Hearing aids may be needed. |
| 3 | 2 - Moderate Impairment | 41-60 dB (better ear) | Able to hear and repeat words spoken in raised voice at 1 meter. | Hearing aids usually recommended. |
| 2 | 3 - Severe Impairment | 61-80 dB (better ear) | Able to hear some words when shouted into better ear. | Hearing aids needed. If no hearing aids available, lip-reading and signing should be taught. |
| 1 | 4 - Profound Impairment Including Deafness | 81 dB or greater (better ear) | Unable to hear and understand even a shouted voice. | Hearing aids may help understanding words. Additional rehabilitation needed. Lip-reading and sometimes signing essential. |

The test stimuli 41 are selected as discrete sound levels within the ranges specified in the WHO grading of hearing impairment. A first test level may be in the first range of about 15 dB to about 25 dB. A second test level may be in the subsequent range of about 30 dB to about 40 dB. A third test level may be in the range of about 45 dB to about 55 dB. A fourth test level may be in the range of about 65 dB to about 75 dB. In some examples, a fifth test level may be in the range of about 81 dB to about 90 dB. The test stimuli 41 are presented at multiple test frequencies comprising 500 Hz, 1000 Hz, 2000 Hz and 4000 Hz. Unlike conventional puting device capable of executing a hearing grading software application 61 according to the teachings herein. After executing the hearing grading software application 61, the user 1 may be presented with a hearing ability score 72 (FIG. 3) from a hearing ability score scale 71, with each hearing ability score (HAS) corresponding to a WHO impairment grade 81 within a WHO grading of hearing impairment scale 80, and hearing aid candidacy indication 79 within hearing aid indication scale 78. It should be understood that the WHO grade may be presented as the hearing ability score. The levels within the hearing grading system may be in the range of about 4-6 discrete levels. Throughout this application, the term "consumer" refers to any person taking the hearing grading test and is interchangeable with other, similar terms, including but not limited to "user," "test subject," etc. The term "hearing aid," is used herein to refer to all types of hearing enhancement devices, including personal sound amplification products (PSAP) generally not requiring a prescription or a medical waiver.

The hearing ability score, 72 for example, is generally based on a computation incorporating the minimal response level at the test frequencies. The computation may incorporate simple averaging, or frequency weighting factors, such as the speech intelligibility index (SII) as per ANSI S3.5 standard. The hearing ability score 72 may be computed using minimal response levels based on only suprathreshold sound levels presented and at step levels of at least 10 dB providing rapid grading of hearing impairment.

Figure 3:
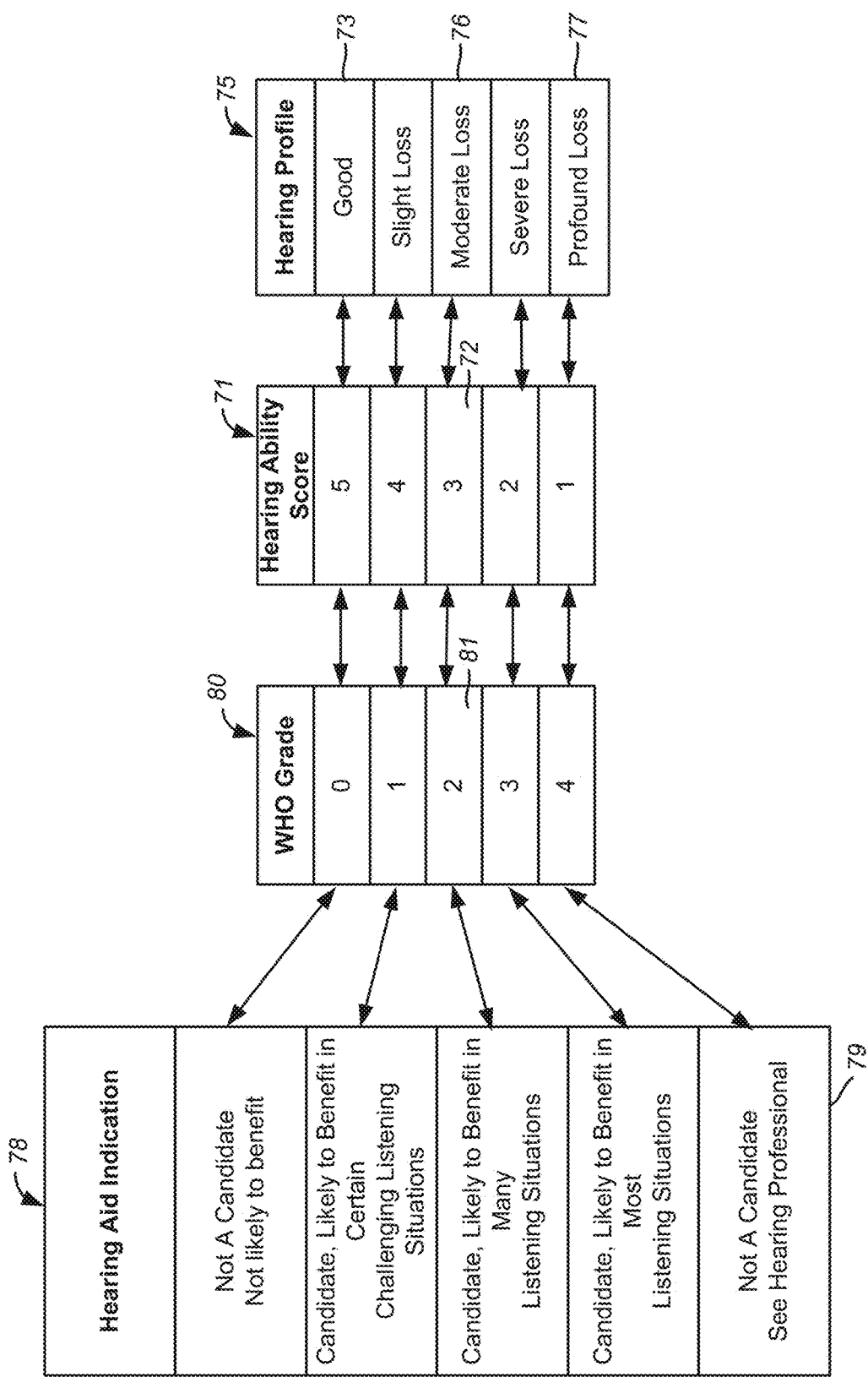
FIG. 3 is a representation of a hearing grading system, including hearing profile categories, hearing ability score scale, corresponding WHO grades, and indication of hearing aid candidacy, according to some examples.

The hearing ability score 72 may be representative of the WHO grading of hearing impairment. The WHO grading of hearing impairment classifies hearing impairment into 5 grades ranging from no or slight hearing problems to profound hearing loss. The 5 WHO grades encompass discrete ranges of hearing impairment and associated recommendation. The WHO guidelines suggest that hearing aids may be needed for those with slight hearing impairment or a higher level of impairment. WHO grades of 2, 3, and 4 are classified as disabling hearing impairment. WHO grades 81 may correspond to a hearing ability score 72, as shown in FIG. 3. In some examples, multiple WHO grades 81 may correspond to a single hearing ability score 72. For example, WHO grades 81 of 0 and 1 may correspond with a hearing ability score 72 of 3 which may be described as minimal loss, WHO grades 81 of 3 and 4 may correspond with a hearing ability score 72 of 1 which may be described as significant loss, and WHO grade 81 of 2 may correspond with a hearing ability score 72 of 2 which may be described as a moderate loss. In some examples, the hearing ability score may be presented as an alphanumeric character. The hearing ability score may be selected from a plurality of alphanumeric characters, each corresponding to a discrete hearing level.

In some embodiments, the acoustic test signal 41 from the computerized hearing grading system 20 may be delivered via an earphone 40 with an eartip 47 (FIG. 8), also referred to here as ear canal "insert," which occludes the ear canal and minimizes the adverse effects of ambient background noise 5 (FIG. 1) present in room environments during the hearing profiling process. The insert 47 is connected to the earphone 40 incorporating a speaker (not shown) within. By presenting calibrated acoustic test signals 41 at suprathreshold levels generally exceeding 15 dB HL, and in combination with an occluding earphone 40, a hearing evaluation may be administered in a typical room environment, as is further described below. In some examples, the earphone insert 47 provides at least 10 decibels of sound attenuation for frequencies between 500 and 4,000 Hz.

In some examples, the acoustic test signal 41 may be delivered via a hearing device 82. The hearing device 82 may be a canal hearing device including a microphone 83, analog-to-digital converter 86, sound processor 87, signal generator 85, digital-to-analog converter 88, and speaker 84 incorporated therein. The hearing device 82 may receive test signal commands from any of the test device 30 and the computing device 10. The hearing device 82 may generate the test stimuli 41 using signal generator 85. The test stimuli 41 may be delivered to the ear 2 using the speaker 84 of the hearing device 82. The hearing device 82 may receive the test signal commands wirelessly, for example using Bluetooth.

Figure 8:
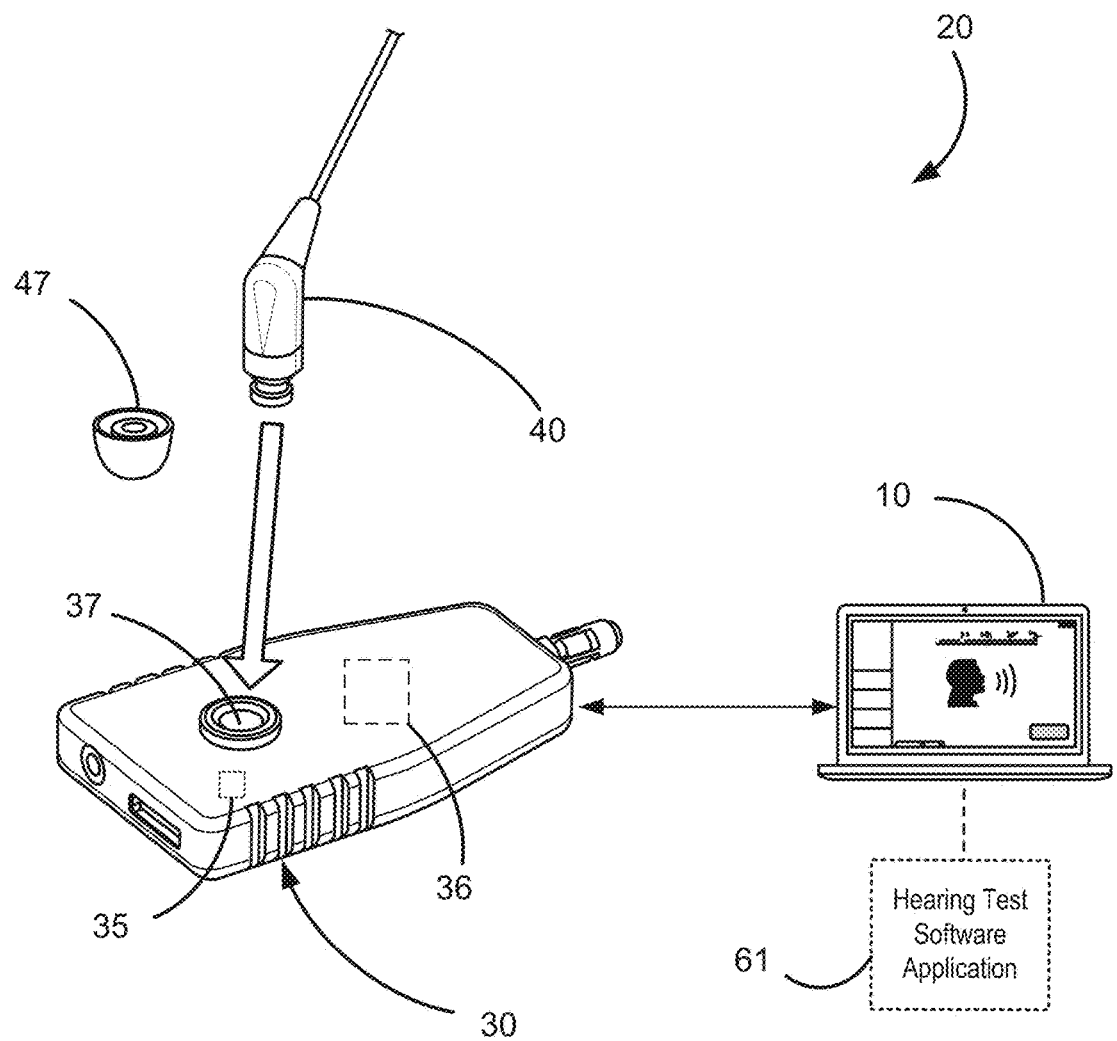
FIG. 8 is a schematic representation of a computerized hearing grading system including a test device incorporating a calibration cavity, according to some examples.

To further mitigate the effects of potentially interfering background noise 5 in certain room environments, a microphone 35 (FIG. 1) may be incorporated within the test device 30 to sense background noise 5 in the vicinity of the user 1. In some examples, as shown in FIG. 8, the microphone 35 may be provided in an acoustic cavity 37 of the test device 30. The acoustic cavity 37 may be shaped to accommodate the earphone 40 and/or a medial (inner) end of the hearing device 82. In some examples, the microphone 35 may be provided elsewhere on the test device 30 or another component of the hearing grading system. The hearing profile test process may then be adjusted according to the background noise 5, for example by delaying or repeating a test stimuli 41 during a noise burst, or by halting the test process in the presence of persistent or excessive background noise. In some examples, an alert may be presented to the user 1 when the background noise 5 exceeds a threshold level.

Figure 10:
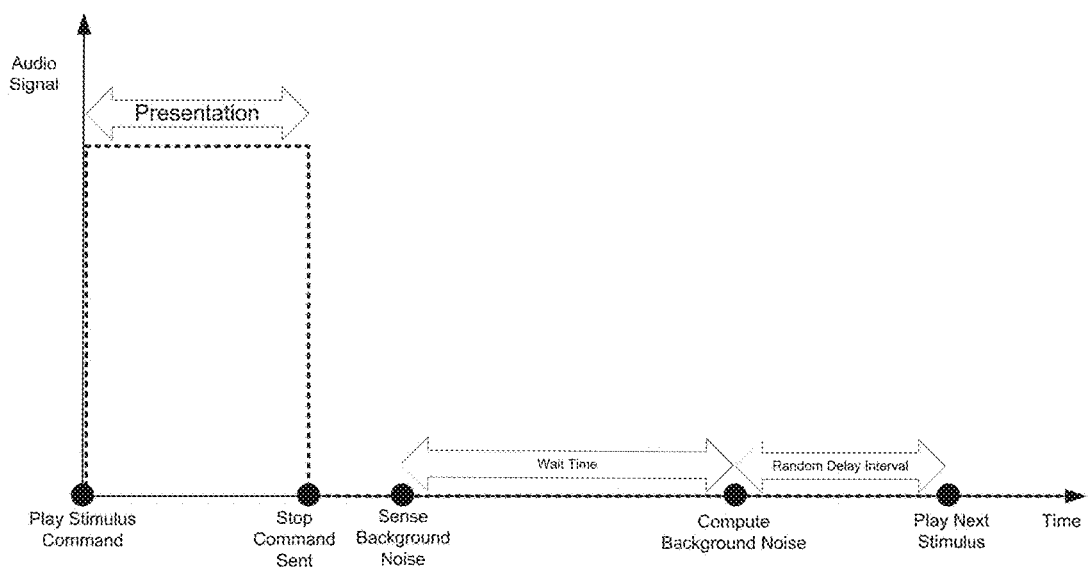
FIG. 10 is a timing diagram of a hearing grading showing test stimulus, noise sensing and delay intervals, according to some examples.

In some examples, background noise sensing is performed before, after or during test signal presentation as shown in FIG. 10. The test system 20 may execute a stop command to stop presenting the test stimulus during a noisy condition. In some examples, the test system 20 may execute the stop command upon detecting a response from the user 1. A random delay interval may be provided to reduce predictably of test signals. In some examples, the random delay interval may be in the range of 1 to 2.5 seconds. After sensing background noise for a predefined amount of time, the hearing test system 20 may provide a random delay interval and compute the background noise level. In some examples, the hearing test system 20 may execute the stop command upon detecting that the background noise level exceeds the maximum allowable level.

Figure 11:
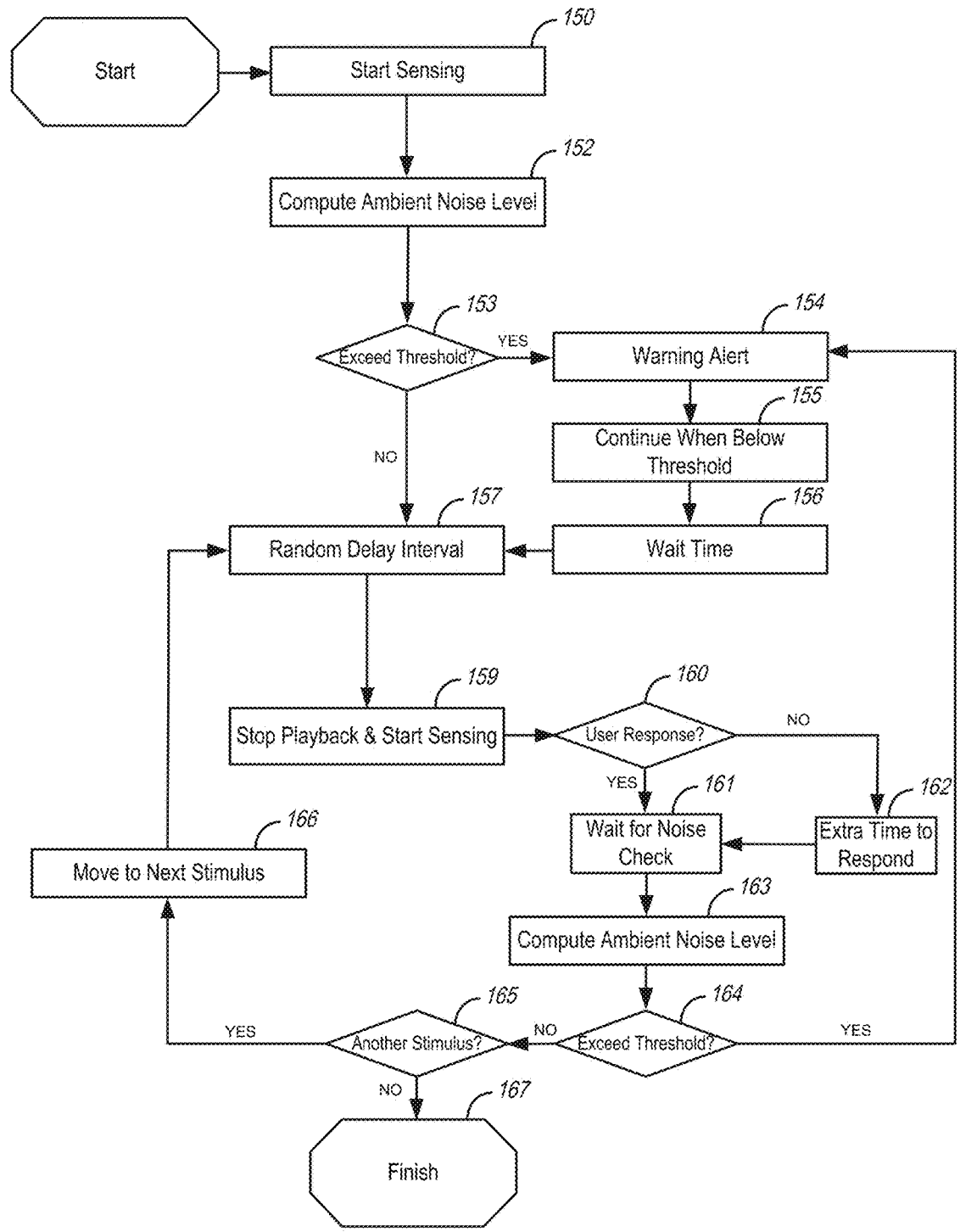
FIG. 11 is a flow chart depicting an example process for sensing background noise during a hearing grading test, according to some examples.

FIG. 11 is a flow chart depicting an example process for sensing background noise (also referred to as ambient noise, background noise, or ambient background noise) during a hearing grading, according to some examples. As shown in the flowchart with operations 150-167, the hearing grading process may be modified in accordance with the background noise sensed. The hearing grading system may start sensing background noise, as shown in operation 150. The ambient noise level may then be computed, as shown in operation 152. A determination may then be made as to whether the ambient noise level exceeds the allowed threshold, as shown in operation 153. If the ambient noise level does exceed the threshold, then a warning alert may be presented, as shown in operation 154. The hearing grading may continue when the ambient noise level is below the noise threshold, as shown in operation 155. There may be a wait time until the ambient noise level is below the threshold, as shown in operation 156. If the ambient noise level does not exceed the threshold in the determination of operation 153, then a random delay interval may be provided, as shown in operation 157. The hearing grading system may then play the next test stimulus. The hearing grading system may then stop playback of the test stimulus and start sensing background noise, as shown in operation 159. A determination may then be made as to whether there was a user response, as shown in operation 160. If there was not a user response, then extra time to respond may be provided, as shown in operation 162. If a user response was detected in the determination of operation 160, then the hearing grading system may wait for an ambient noise check, as shown in operation 161. The hearing grading system may then computer an ambient noise level, as shown in operation 163. A determination may then be made as to whether the ambient noise level exceeds a noise threshold, as shown in operation 164. If yes, then the process may return to operation 154 and present a warning alert to the user. If the ambient noise level does not exceed the threshold in the determination of operation 164, then a determination may be made as to whether there is another test stimulus to present, as shown in operation 165. If yes, then the hearing grading system may move to the next stimulus, as shown in operation 166, and return to operation 157 and provide a random delay interval. If there is not another stimulus in the determination of operation 165, then the process may finish, as shown in operation 167.

Figure 9:
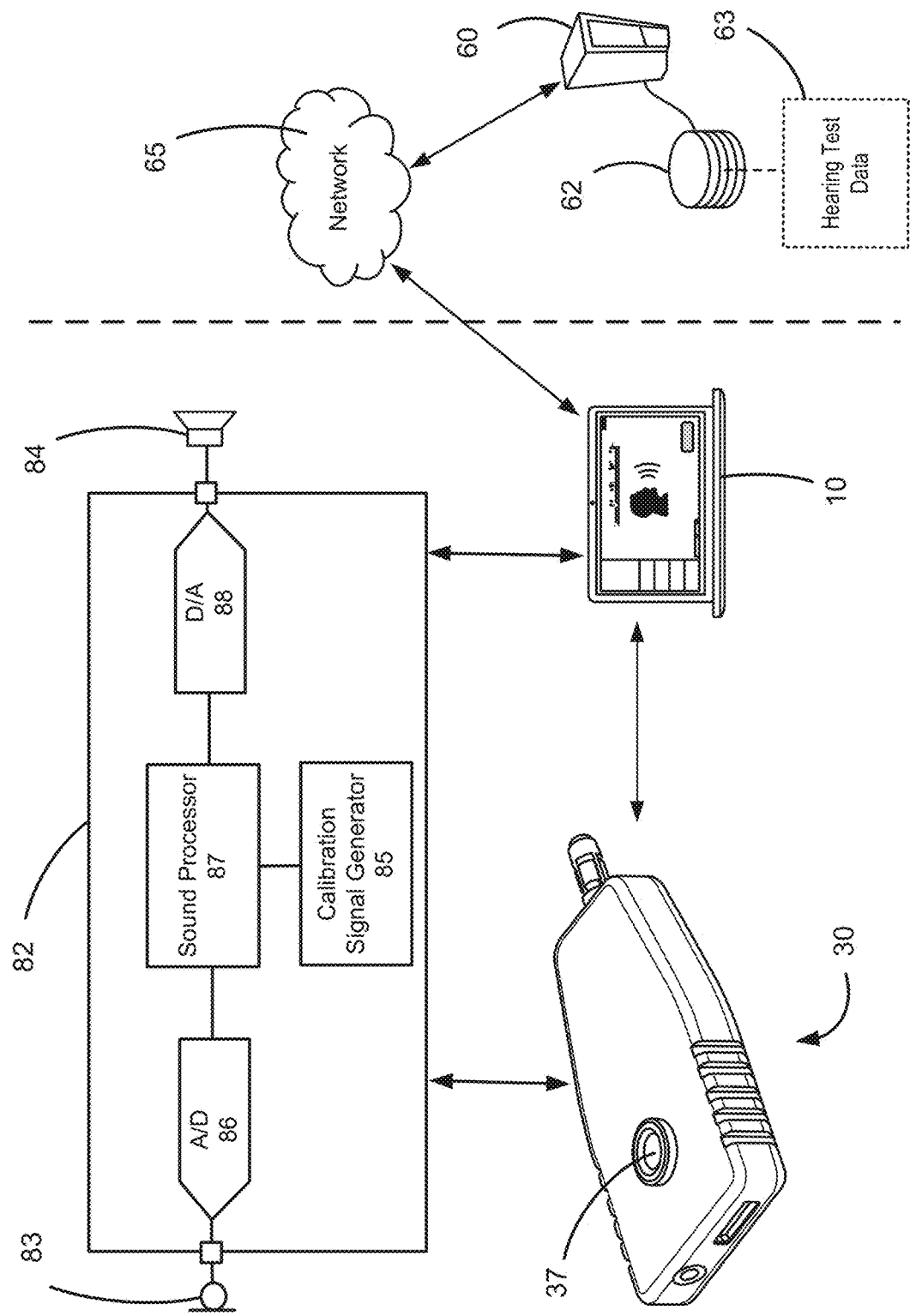
FIG. 9 is a schematic representation of an online hearing grading system including a remote database for hosting hearing test data, according to some examples.

In some examples, the computerized hearing grading system 20 is designed primarily for self-administration. However, it should be understood that assistance may be provided for certain individuals, for example those with limitations related to aging, heath condition, or mental capacity. A non-expert health provider may also administer the test to others using the hearing test system 20 and method. The test device 30, in some embodiments, includes a USB interface 38 for interfacing with, and control by, a personal computer 10, and in some cases for streaming of digital audio representing test signals or audio instructions to the user from the personal computer 10. Digital audio files representing test stimuli, as well as calibration data associated with calibrated test stimuli, may be stored within the test device 30, within the client personal computer 10, on a remote database 62 (FIG. 9), or generally anywhere on the Internet "cloud" 65 (FIG. 9). The test device 30 houses an audio signal generator 36 (also referred to herein as "digital audio system"), and includes programmable audio amplifiers to provide calibrated test audio signals 31. The digital audio system may be configured to provide calibrated audio signals 31 regardless of the computer platform used by the consumer 1. This allows for predictable audio characteristics conforming to accepted standards, for example as per ANSI/ASA 3.6.

In some examples, one or more natural sounds may be employed as test stimuli 41 to engage the consumer with sounds relevant to the human hearing experience. In contrast to traditional methods, which employ tonal sounds, natural sounds represent sounds audible in normal listening experiences, such as human speech, music, drum snare, animal sounds, bird chirp, wheel squeak, etc.

Figure 4:
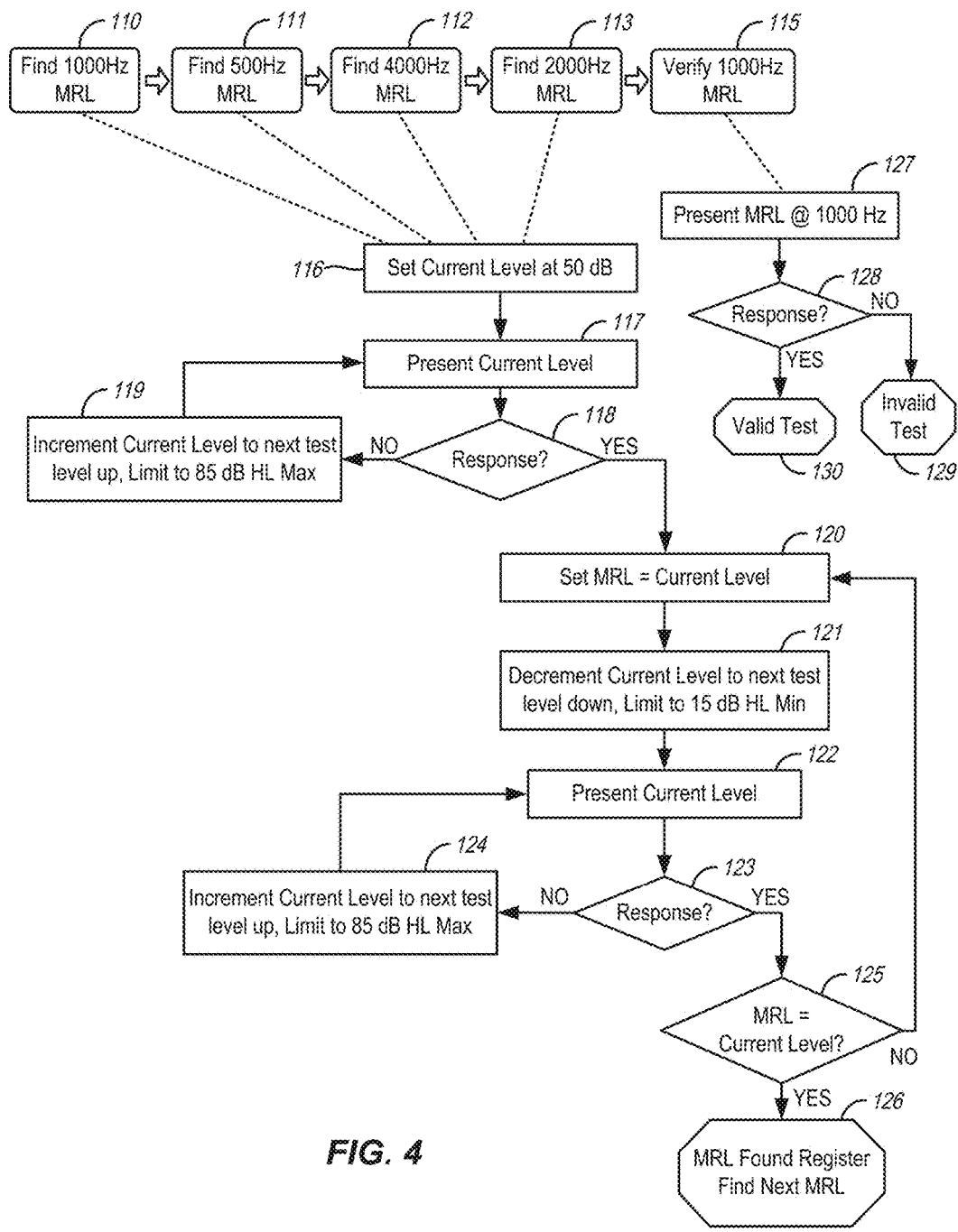
FIG. 4 is a flow chart depicting a simplified example process for automatically presenting test signals and determining minimum response levels, according to some examples.

FIG. 4 shows a simplified example flowchart for an automatic determination of the hearing grading, and specifically the steps of determining the minimum response level (MRL) of the consumer 1 within the range of the suprathreshold sound levels presented. As shown in the flowchart with operations 110-130, starting with determining MRL at 1000 Hz. (operation 110), a signal level of 50 dB HL may be initially set (operation 116) and test stimuli 41 is presented at 50 dB HL (operation 117) to the consumer 1. The response from the consumer 1 is then determined by operation 118 and if no response is registered by the computerized hearing grading system 20 within a time window, typically 1 to 1.5 seconds from the end of the stimuli period, the "current level" of the test stimuli 41 is incremented to the next test level up, up to a maximum level of 85 dB HL for example (operation 119) and the test stimuli 41 is then presented to consumer 1 at the increased level (operation 117). When a response is detected in operation 118, an MRL value is recorded (operation 120) for subsequent verification by operations 120-126 whereby the test signal level is decremented to the next lower test level (operation 121) and presented (operation 122) for response determination (operation 123). If a response is not registered at operation 123, the test stimuli level is incremented to the next test level up (operation 124) and the test stimuli is presented (operation 122) with the increased level, and the process is repeated if necessary, until a response is registered at operation 123. The MRL for a test frequency is considered "found" (operation 126) generally when the computerized hearing grading system 20 detects two consumer responses at the same presentation level as determined by operation 125, which compares a currently registered response level with a previously recorded MRL. If the current response level does not match the previously recorded MRL, a new MRL value is set and recorded (operation 120) and the signal level is decremented to the next test lower test level (operation 121) until an MRL is determined (operation 125). In the some examples, the step size for consecutive test presentations is within the range of 10-25 dB.

The process for determining MRLs for all test frequencies (operations 110-114) may be sequenced as in shown in FIG. 4, or interleaved (not shown), either randomly or at a predetermined interleave sequence. Interleaving may minimize predictability of test process sequence by the consumer 1 and may improve the reliability of the test. A final verification process (operation 115) at one frequency, typically at 1000 Hz, is preferably administered to assess the reliability of the user's responses. For example by re-presenting a 1000 Hz test stimuli 41 (operation 127) at the MRL previously determined in operation 110, and determining if the consumer 1 is responding consistently at this level (operation 128), and to determine either a reliable 'valid test' (operation 130) or inconsistent "invalid test" (operation 129). It should be understood that variations of the aforementioned example hearing evaluation process and algorithm thereof are possible and may be advantageous.

In an online embodiment of the hearing evaluation method of the present invention shown in FIG. 10, a hearing test software application 61 may be at least partially hosted by a memory 62 of a remote server 60 and executed locally by a personal computer 10. The personal computer 10 may be connected online to the remote server 60 via the Internet 65. The results of the hearing evaluation, including the hearing ability score, and/or other hearing test data 63 may be stored in a remote database 62.

Figure 5:
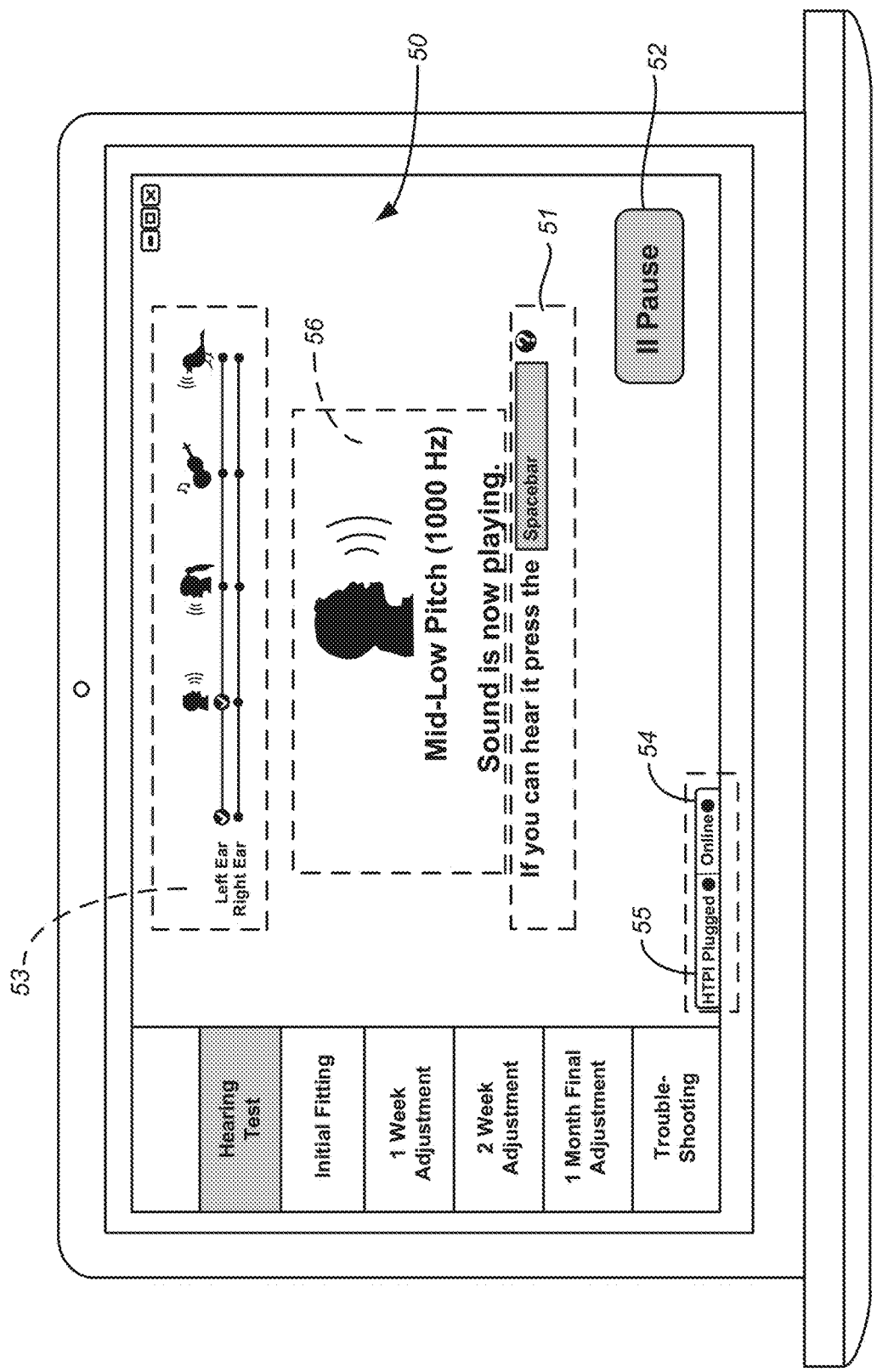
FIG. 5 is a view of a hearing grading user interface from a software application, with test in progress, according to some examples.

FIG. 5 shows an example user interface (UI) 50 for an online embodiment of the hearing evaluation method, employing a software application (e.g., a web application) or browser to execute a hearing profile software application. The UI 50 shows UI elements, including user instructions 51, test pause control 52, test presentation status 56, test process status 53, online connection status 54, and test device connection status 55. In this embodiment of the user interface 50, the user 1 is generally instructed to listen to the calibrated test sounds 41 presented and press the space bar of the keyboard 11 (or a key on the touch screen 12) when the sound 41 is heard. In one embodiment, the is a client application, which provides access to, and control of, the test device 30. The client application may be downloadable by the user online, for example during an online registration of the test device 30.

Figure 6:
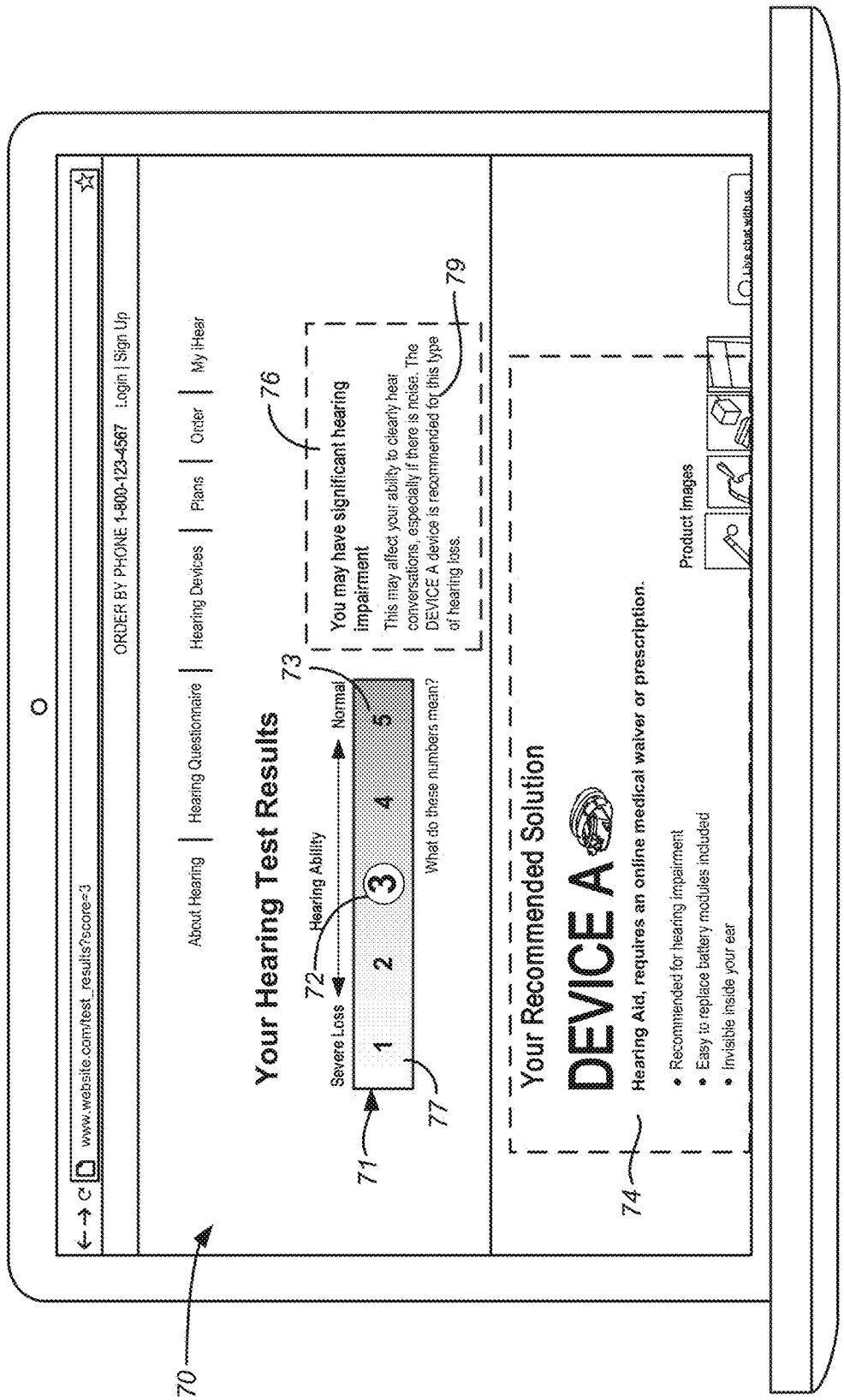
FIG. 6 is a front view of a hearing grading scale and score presented on a software application user interface, indicating hearing aid candidacy and a hearing aid recommendation, according to some examples.
Figure 7:
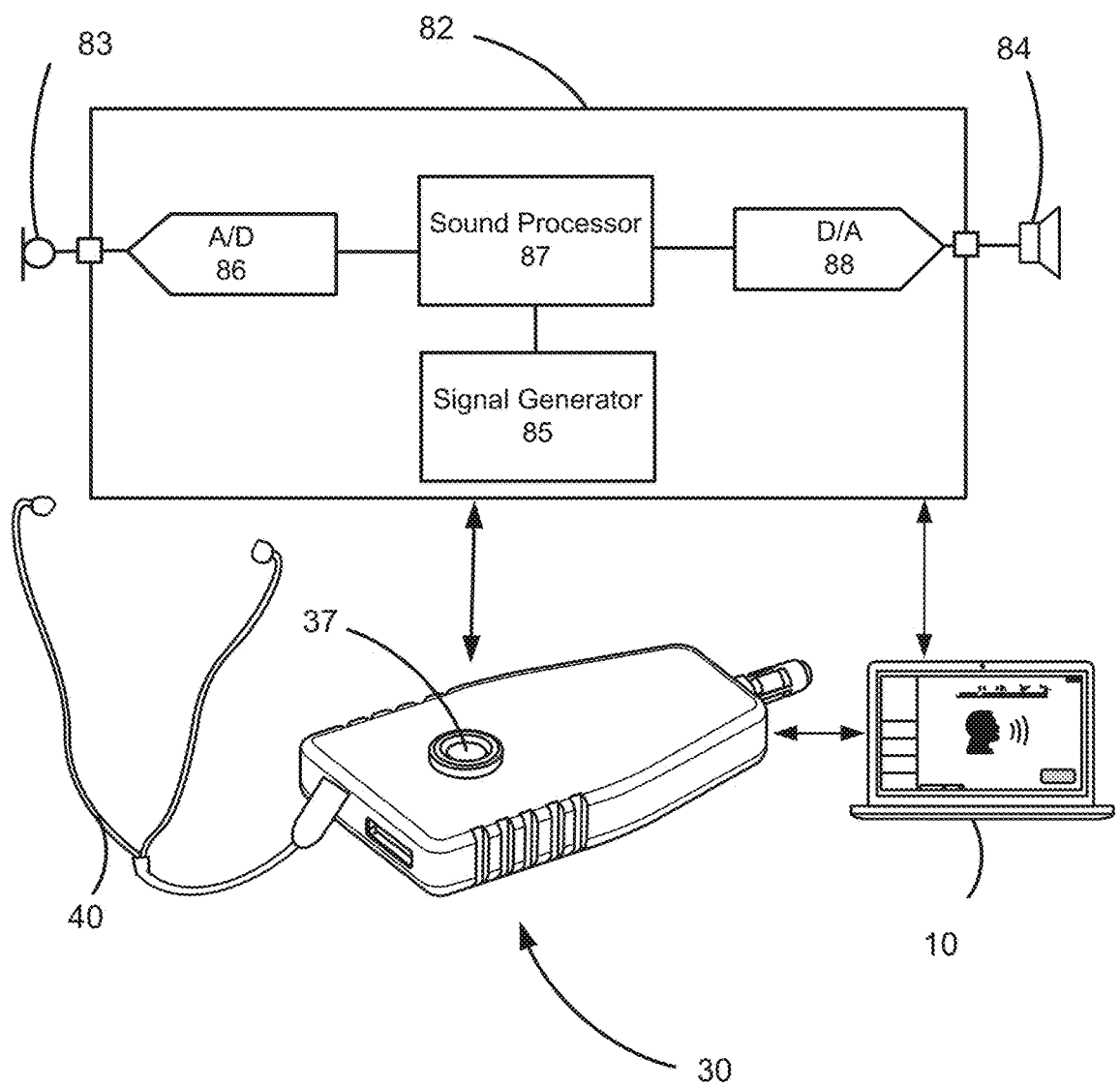
FIG. 7 is a schematic representation of a computerized hearing grading system including a test device and computing device in communication with a hearing device to perform a hearing grading, according to some examples.

FIG. 6 shows an example representation of the hearing profile scoring UI 70, showing hearing ability score 72, hearing ability score scale 71, and hearing ability statement 76 and hearing aid indication statement 79. Contrasting the hearing profiling system disclosed herein with standard audiogram reports, which display the sensitivity of hearing from −10 to 110 dB in 5 dB steps and in a reverse order without indicating hearing ability or candidacy, the hearing ability score 72 and corresponding hearing ability statement 76 and hearing aid candidacy statement 79, indicates the general ability to hear from "Good" 73 to "Profound" 77, suggesting professional assessment and/or intervention. Hearing aid candidacy 79 may be determined at least partially from the hearing ability score, and in some cases other factors may also contribute.

According to various alternative embodiments, suitable variations of the scoring system and method and corresponding indications may be made, such as reversing the order of the scoring scale 71, with level 0 representing "Good" hearing and the highest level representing "Profound Loss." Alternatively, alphanumeric character representation, such A, B, C, etc., may be used to represent the hearing ability. In some examples, the scoring levels may be limited to 5 categories. The web application page UI 70 of FIG. 6 also shows a hearing aid recommendation section 74, describing product and pricing options to the consumer.

In contrast to conventional audiometric test methods and reports, the systems and methods disclosed herein simplify and expedite the test process by eliminating various redundancies and limiting the hearing evaluation to test signals relevant to hearing aid candidacy and hearing aid indication, generally at levels above 15 dB HL and frequencies above 500 Hz and up to 4,000 Hz. By eliminating testing below 500 Hz, the adverse effects of low frequency noise commonly present in room environments may be substantially mitigated.

Experiment

The following experiment was conducted to assess and validate the hearing grading method using the iHearTest, a computerized hearing grading system, in normal room environments according to the teachings disclosed herein. Sound measurements were taken in a room with a personal computer and test instruments used to conduct the experiment. The measurements for the computerized hearing grading system were obtained using the iHearTest system using the iHearTest software application. For the measurements for the computerized hearing grading system, fan noise from the computers and street noise were noticeably audible by unoccluded ears. Measurements obtained using the iHearTest were compared to measurements obtained using standard audiological equipment, including a Madsen OB822 Clinical Audiometer with Ear3A insert earphones and a Maico MA42 portable audiometer with TDH39 headphones. The measurements using current practice audiometers were taken while the subject was in a standard sound isolation room. This experiment is reported here by way of example and to facilitate understanding and appreciation of the system and methods described herein. Inclusion of this experiment here is in no way intended to represent that all experiments performed did or will achieve like results.

15 subjects with 30 ears in total were studied. At least 5 subjects had a hearing loss of 45 dB HL or worse at one or more frequencies in one or more ears. Each subject was administered a pure tone audiogram by a licensed hearing care professional at 250, 500, 1000, 1500, 2000, 3000, 4000, 6000, and 8000 Hz using insert earphones in a sound isolation room. After obtaining audiogram results for each ear, the hearing grading was determined for each ear.

The subjects were then tested using the iHearTest system comprising a personal computer, a USB test device (iHearTestUSB), and a hearing test application (iHearTest app version A.02). The hearing grading of the iHearTest was conducted outside of the sound isolation room in an office environment. Hearing ability scores were computed and recorded. The test levels presented by the iHearTest were at 25, 35, 50, 70 and 85 dB HL, at 500, 1000, 2000 and 4000 Hz. The step levels ranged from 10 to 20 dB.

As shown in Table 2, the hearing ability scores (HAS) generated using the iHearTest was substantially equivalent to the WHO grading results obtained by conventional audiometry (AUD) in the subjects tested. Corresponding HAS Scores for the WHO grade are provided in Table 2 for direct comparison to the HAS of the iHearTest. The iHearTest results agreed with the WHO grades computed using conventional audiometry in 90% of the ears tested. The hearing grading for both the iHearTest method and conventional audiometry were computed using equal weighted averaging. The 10% test result variability was consistent with variability obtained by two different audiometer settings (AUD #1 and AUD #2), as shown in Table 3. Table 4 shows the iHearTest results in agreement for determining disabling hearing impairment (WHO grades 2, 3 and 4) in 100% of the cases for the 15 subjects tested. It should be noted here that hearing grading results reported herein were analyzed and tabulated for individual ears.

Thus, the hearing grading system including methods disclosed herein was able to accurately grade hearing impairment and substantially in agreement with WHO grading with a substantially reduced set of test stimuli and without resorting to audiogram testing, a sound isolation room or relatively expensive audiological equipment.

TABLE 2

| | 1000 Hz | | 4000 Hz | | | | | |
|---|---|---|---|---|---|---|---|---|
| #1 Right | 15 | 10 | 10 | 15 | 0 | 5 | 5 | Yes |
| #1 Left | 10 | 5 | 5 | 20 | 0 | 5 | 5 | Yes |
| #2 Right | 10 | 10 | 5 | 5 | 0 | 5 | 5 | Yes |
| #2 Left | 10 | 5 | 15 | 5 | 0 | 5 | 5 | Yes |
| #3 Right | 15 | 15 | 15 | 20 | 0 | 5 | 5 | Yes |
| #3 Left | 15 | 5 | 5 | 10 | 0 | 5 | 5 | Yes |
| #4 Right | 20 | 15 | 15 | 45 | 0 | 5 | 5 | Yes |
| #4 Left | 15 | 15 | 30 | 50 | 1 | 4 | 4 | Yes |
| #5 Right | 10 | 10 | 10 | 15 | 0 | 5 | 5 | Yes |
| #5 Left | 5 | 10 | 15 | 5 | 0 | 5 | 5 | Yes |
| #6 Right | 20 | 15 | 30 | 50 | 1 | 4 | 5 | No |
| #6 Left | 20 | 20 | 30 | 55 | 1 | 4 | 4 | Yes |
| #7 Right | 5 | 5 | 5 | 5 | 0 | 5 | 5 | Yes |
| #7 Left | 0 | 5 | 0 | 10 | 0 | 5 | 5 | Yes |
| #8 Right | 15 | 20 | 15 | 15 | 0 | 5 | 4 | No |
| #8 Left | 20 | 15 | 15 | 20 | 0 | 5 | 5 | Yes |
| #9 Right | 15 | 20 | 15 | 15 | 0 | 5 | 5 | Yes |
| #9 Left | 20 | 15 | 5 | 5 | 0 | 5 | 5 | Yes |
| #10 Right | 20 | 15 | 15 | 15 | 0 | 5 | 5 | Yes |
| #10 Left | 20 | 10 | 20 | 25 | 0 | 5 | 5 | Yes |
| #11 Right | 10 | 15 | 10 | 10 | 0 | 5 | 5 | Yes |
| #11 Left | 10 | 10 | 5 | 10 | 0 | 5 | 5 | Yes |
| #12 Right | 35 | 40 | 55 | 60 | 2 | 3 | 3 | Yes |
| #12 Left | 30 | 35 | 45 | 60 | 2 | 3 | 3 | Yes |
| #13 Right | 10 | 15 | 15 | 15 | 0 | 5 | 5 | Yes |
| #13 Left | 10 | 10 | 20 | 15 | 0 | 5 | 5 | Yes |
| #14 Right | 45 | 45 | 50 | 65 | 2 | 3 | 3 | Yes |
| #14 Left | 55 | 50 | 55 | 60 | 2 | 3 | 2 | No |
| #15 Right | 20 | 15 | 20 | 60 | 1 | 4 | 4 | Yes |
| #15 Left | 15 | 20 | 20 | 15 | 0 | 5 | 5 | Yes |

Percent Agreement of iHearTest score with Audiogram-based WHO grading: 90%

TABLE 3

| Subject | AUD #1 WHO Grade | AUD #2 WHO Grade | Agreement |
|---|---|---|---|
| #1 Right | 0 | 0 | Yes |
| #1 Left | 0 | 0 | Yes |

TABLE 3-continued

| Subject | AUD #1 WHO Grade | AUD #2 WHO Grade | Agreement |
|---|---|---|---|
| #2 Right | 0 | 0 | Yes |
| #2 Left | 0 | 0 | Yes |
| #3 Right | 0 | 0 | Yes |
| #3 Left | 0 | 0 | Yes |
| #4 Right | 0 | 0 | Yes |
| #4 Left | 1 | 0 | No |
| #5 Right | 0 | 0 | Yes |
| #5 Left | 0 | 0 | Yes |
| #6 Right | 1 | 0 | No |
| #6 Left | 1 | 1 | Yes |
| #7 Right | 0 | 0 | Yes |
| #7 Left | 0 | 0 | Yes |
| #8 Right | 0 | 0 | Yes |
| #8 Left | 0 | 0 | Yes |
| #9 Right | 0 | 0 | Yes |
| #9 Left | 0 | 0 | Yes |
| #10 Right | 0 | 0 | Yes |
| #10 Left | 0 | 0 | Yes |
| #11 Right | 0 | 0 | Yes |
| #11 Left | 0 | 0 | Yes |
| #12 Right | 2 | 2 | Yes |
| #12 Left | 2 | 2 | Yes |
| #13 Right | 0 | 0 | Yes |
| #13 Left | 0 | 0 | Yes |
| #14 Right | 2 | 2 | Yes |
| #14 Left | 2 | 2 | Yes |
| #15 Right | 1 | 0 | No |
| #15 Left | 0 | 0 | Yes |

Percent Agreement: 90%

TABLE 4

| | iHearTest | Disabling Impairment | |
|---|---|---|---|
| #1 Right | No | No | Yes |
| #1 Left | No | No | Yes |
| #2 Right | No | No | Yes |
| #2 Left | No | No | Yes |
| #3 Right | No | No | Yes |
| #3 Left | No | No | Yes |
| #4 Right | No | No | Yes |
| #4 Left | No | No | Yes |
| #5 Right | No | No | Yes |
| #5 Left | No | No | Yes |
| #6 Right | No | No | Yes |
| #6 Left | No | No | Yes |
| #7 Right | No | No | Yes |
| #7 Left | No | No | Yes |
| #8 Right | No | No | Yes |
| #8 Left | No | No | Yes |
| #9 Right | No | No | Yes |
| #9 Left | No | No | Yes |
| #10 Right | No | No | Yes |
| #10 Left | No | No | Yes |
| #11 Right | No | No | Yes |
| #11 Left | No | No | Yes |
| #12 Right | Yes | Yes | Yes |
| #12 Left | Yes | Yes | Yes |
| #13 Right | No | No | Yes |
| #13 Left | No | No | Yes |
| #14 Right | Yes | Yes | Yes |
| #14 Left | Yes | Yes | Yes |
| #15 Right | No | No | Yes |
| #15 Left | No | No | Yes |

Percent Agreement of iHearTest score with Audiogram-based WHO grading: 100%

Although examples of the invention have been described herein, variations and modifications of this exemplary embodiment and method may be made without departing from the true spirit and scope of the invention. Thus, the above-described embodiments of the invention should not be viewed as exhaustive or as limiting the invention to the precise configurations or techniques disclosed. Rather, it is intended that the invention shall be limited only by the appended claims and the rules and principles of applicable law.

What is claimed is:

1. A method of administering a hearing grading for a user, the method comprising:
   providing sequences of test stimuli to an ear of the user, the test stimuli comprising test stimuli levels within a suprathreshold range of 15 dB to 95 dB HL, each of the sequences comprising test stimuli at test frequencies comprising 500, 1000, 2000 and 4000 Hz, wherein the test stimuli levels comprise:
      a first test level in the range of 15-25 dB HL;
      a second test level in the range of 30-40 dB HL;
      a third test level in the range of 45-55 dB HL; and
      a fourth test level in the range of 65-75 dB HL;
   registering, using a computerized hearing grading system, a minimal response level for the test stimuli presented at each of the test frequencies;
   computing a hearing ability score based on an average of the minimal response levels for the test frequencies tested only within the suprathreshold range, wherein the hearing ability score is representative of the World Health Organization (WHO) grading of hearing impairment; and
   presenting the hearing ability score to the user by the computerized hearing grading system.

2. The method of claim 1, wherein the test stimuli levels further comprise a fifth test level in the range of 81-95 dB.

3. The method of claim 1, wherein step levels of test stimuli within a sequence presented by the computerized hearing grading system are nonuniform.

4. The method of claim 1, further comprising sensing ambient background noise by a microphone associated with the computerized hearing grading system.

5. The method of claim 4, further comprising presenting an alert to the user when the ambient noise sensed by the microphone is above a predefined threshold noise level.

6. A method of grading hearing according to the WHO grading of hearing impairment, the method comprising:
   providing test stimuli to an ear of a non-expert user, wherein the test stimuli are provided at test stimuli levels of at least 15 dB HL at test frequencies comprising 500, 1000, 2000 and 4000 Hz, and wherein the test stimuli levels are incremented at step levels of 10 dB or greater;
   registering, using a computerized hearing grading system, a minimal response level for the test stimuli presented at each of the test frequencies;
   computing a hearing ability score based on an average of the minimal response levels for the test frequencies tested only within a suprathreshold range above 15 dB HL, wherein the hearing ability score is representative of the WHO grading of hearing impairment; and
   presenting the hearing ability score to the consumer by the computerized hearing grading system.

7. The method of claim 6, wherein the test stimuli levels comprise:
   a first test level in the range of 15-25 dB HL;
   a second test level in the range of 30-40 dB HL;
   a third test level in the range of 45-55 dB HL; and
   a fourth test level in the range of 65-75 dB HL.

8. The method of claim 7, wherein the test stimuli levels further comprises a fifth level in the range of 81-95 dB.

9. The method of claim 6, wherein the computerized hearing grading system comprises any of a personal computer, a smart phone and a tablet.

10. The method of claim 6, wherein the hearing grading system comprises any of an earphone and a hearing device configured to deliver the test stimuli to an ear of the user.

11. The method of claim 10, wherein the earphone, the hearing device, or both are configured to attenuate ambient background noise by at least 10 dB across the audiometric frequency range of 500 to 4,000 Hz.

12. The method of claim 10, wherein the earphone comprises an insert configured to occlude the ear canal and attenuate ambient background noise.

13. The method of claim 6, wherein the hearing ability score is selected from a plurality of discrete levels, the plurality of discrete levels comprising a range of four to six discrete levels.

14. The method of claim 6, wherein the computerized hearing grading system is communicatively coupled to a remote database hosting hearing test data.

15. The method of claim 14, wherein a hearing test software application executed by the computerized hearing grading system is configured to administer the hearing grading for the user using the hearing test data.

16. The method of claim 15, further comprising executing the hearing test software application from any of a standalone application, a web application, or an Internet browser.

17. The method of claim 6, further comprising sensing ambient background noise by a microphone associated with the computerized hearing grading system.

18. The method of claim 6, wherein the test stimuli include at least one natural sound.

19. The method of claim 6, wherein the average is computed using equal weighted averaging.

20. The method of claim 6, wherein the average is computed using a speech articulation index weighting.

21. The method of claim 6, further comprising presenting a hearing aid candidacy to the user at least partially based on the WHO grading of hearing impairment.

22. The method of claim 6, further comprising producing masking sound to a non-test ear.

23. A method of automatically grading a hearing ability, the method comprising:
presenting a sequence of acoustic test stimuli at suprathreshold sound levels of at least 15 dB HL by a computerized hearing grading system at a plurality of test frequencies within an audiometric frequency range between 500 and 4,000 Hz;
presenting the sequence of acoustic test stimuli at non-uniform step levels, wherein each step level for acoustic test stimuli is within the range of 10-25 dB;
registering a minimal response level of a consumer at each test frequency; and
computing a hearing ability score based on the consumer's minimal response level at each test frequency, wherein the hearing ability score is representative of the WHO grading of hearing impairment.

24. A method of determining a hearing aid candidacy of a consumer by a hearing grading system, the method comprising:
presenting test stimuli at test levels of at least 15 dB HL at multiple test frequency bands to an ear of the consumer using an earphone, wherein the earphone is configured to attenuate ambient background noise, wherein the test levels comprise:
a first test level in the range of 15-25 dB HL;
a second test level in the range of 30-40 dB HL;
a third test level in the range of 45-55 dB HL; and
a fourth test level in the range of 65-75 dB HL;
registering a minimum response level of the consumer at each of a plurality of test frequencies selected from the multiple test frequency bands;
computing a hearing ability score based on the minimum response levels at the plurality of test frequencies; and
indicating hearing aid candidacy to the consumer, based at least in part on the WHO grading of hearing impairment.

25. A method of online hearing assessment of a consumer, the method comprising:
executing a hearing assessment application by a personal computer, wherein the hearing assessment application is at least partially hosted by a remote server;
delivering a test audio signal to an earphone from an audio generator communicatively coupled to the personal computer;
delivering a calibrated acoustic output signal from the earphone at multiple suprathreshold test levels, wherein the test levels comprise:
a first test level in the range of 15-25 dB HL;
a second test level in the range of 30-40 dB HL;
a third test level in the range of 45-55 dB HL; and
a fourth test level in the range of 65-75 dB HL;
registering a minimal response of the consumer at multiple frequency bands by the personal computer; and
presenting to the consumer a computed hearing ability score based on the minimal response level of the consumer at each test frequency band from the multiple frequency bands, wherein the hearing ability score is representative of the WHO grading of hearing impairment.

26. A hearing profile test system, comprising;
an earphone configured to receive test audio signals to produce calibrated test stimuli for delivery to an ear canal at suprathreshold sound levels, wherein the earphone is configured to occlude the ear canal and attenuate ambient background sound, wherein the suprathreshold test levels comprise:
a first test level in the range of 15-25 dB HL;
a second test level in the range of 30-40 dB HL;
a third test level in the range of 45-55 dB HL; and
a fourth test level in the range of 65-75 dB HL;
a test device incorporating an audio signal generator configured to produce the test audio signals; and
a computer-readable medium comprising executable instructions, which when executed by a computer communicatively coupled to the test device cause the computer to compute a hearing ability score which is representative of the WHO grading of hearing impairment.

27. The hearing profile test system of claim 26, further comprising a microphone configured to sense ambient noise.

28. The hearing profile test system of claim 26, wherein the test device comprises a USB interface.

29. The hearing profile test system of claim 26, wherein the computer-readable medium is configured for execution on any of a personal computer, a smart phone, and a tablet.

30. A system for online hearing evaluation, the system comprising;
a test device including an audio signal generator configured to produce an audio signal output;
an earphone configured to receive the audio signal output from the test device and to deliver suprathreshold test stimuli exceeding 15 dB HL to a user's ear at multiple test levels, wherein the test levels comprise:

a first test level in the range of 15-25 dB HL;
a second test level in the range of 30-40 dB HL;
a third test level in the range of 45-55 dB HL; and
a fourth test level in the range of 65-75 dB; and computer-readable medium comprising instructions for a hearing test application, wherein the instructions for the hearing test application include instruction which when executed by one or more processor cause the one or more processors to receive an indication of a minimum response levels of the user to the test stimuli and compute a hearing ability score based on the minimum response level, the instructions for the hearing test application further comprising instructions for displaying a computed hearing ability score which is representative of the WHO grading of hearing impairment.

31. The system of claim 30, wherein the instructions for the hearing test application include instructions configured to be executed by one or more processors of a personal computer, a smart phone, or a tablet, and configured to cause the computer, smart phone, or tablet, to transmit the indication of a minimum response level to a remote server and receive the computed hearing ability score from the server, wherein the hearing ability score computed based on the minimum response level of the user.

32. The system of claim 30, further comprising a microphone configured to sense ambient noise.

* * * * *